(12) United States Patent
Wopereis et al.

(10) Patent No.: US 11,064,722 B2
(45) Date of Patent: Jul. 20, 2021

(54) RISK OF ALLERGY AND NUTRITION TO REDUCE THAT RISK

(71) Applicant: N.V. NUTRICIA, Zoetermeer (NL)

(72) Inventors: Harm Johannes Wopereis, Utrecht (NL); Jan Knol, Utrecht (NL)

(73) Assignee: N.V. Nutricia, Zoetermeer (NL)

( * ) Notice: Subject to any disclaimer, the term of this patent is extended or adjusted under 35 U.S.C. 154(b) by 115 days.

(21) Appl. No.: 16/308,378

(22) PCT Filed: Jun. 12, 2017

(86) PCT No.: PCT/EP2017/064233
§ 371 (c)(1),
(2) Date: Dec. 7, 2018

(87) PCT Pub. No.: WO2017/212064
PCT Pub. Date: Dec. 14, 2017

(65) Prior Publication Data
US 2019/0133172 A1  May 9, 2019

(30) Foreign Application Priority Data

Jun. 10, 2016  (EP) .................................... 16174039

(51) Int. Cl.
*A23L 33/135* (2016.01)
*C12Q 1/04* (2006.01)
(Continued)

(52) U.S. Cl.
CPC ............ *A23L 33/135* (2016.08); *A23L 33/21* (2016.08); *A23L 33/40* (2016.08); *A61K 35/741* (2013.01);
(Continued)

(58) Field of Classification Search
CPC ........ A23L 33/135; A23L 33/21; A23L 33/40; A61K 35/741; G01N 2800/24; G01N 2800/38; G01N 2800/50
(Continued)

(56) References Cited

U.S. PATENT DOCUMENTS

| 2004/0131659 A1 | 7/2004 | Gibson et al. |
| 2005/0288250 A1 | 12/2005 | Rautonen et al. |

(Continued)

FOREIGN PATENT DOCUMENTS

| CN | 101496819 A | * | 1/2008 |
| CN | 101496819 A | | 8/2009 |

(Continued)

OTHER PUBLICATIONS

Marks, Jay W. "Stool Acidity Test", p. 1, https://www.medicinenet.com/stool_acidity_test/article.htm (Year: 1996).*

(Continued)

*Primary Examiner* — Helen F Heggestad
(74) *Attorney, Agent, or Firm* — N.V. Nederlandsch Octrooibureau; Catherine A. Schultz; Tamara C. Stegmann

(57) ABSTRACT

A method to predict the risk of eczema is provided based on differences in the development of microbiota and its metabolites in healthy infants and infants that develop eczema, and nutritional remedies based on this finding, in the form of lactate utilizing bacteria and fibres stimulating lactate utilizing bacteria.

6 Claims, 1 Drawing Sheet

(51) Int. Cl.
 *A23L 33/00* (2016.01)
 *A23L 33/21* (2016.01)
 *A61K 35/741* (2015.01)

(52) U.S. Cl.
 CPC ........... *C12Q 1/04* (2013.01); *G01N 2800/24* (2013.01); *G01N 2800/38* (2013.01); *G01N 2800/50* (2013.01)

(58) Field of Classification Search
 USPC .................................. 426/62, 648, 658, 801
 See application file for complete search history.

(56) References Cited

U.S. PATENT DOCUMENTS

| | | |
|---|---|---|
| 2010/0069320 A1* | 3/2010 | Speelmans |
| 2010/0322904 A1 | 12/2010 | Scholten et al. |
| 2014/0170126 A1 | 6/2014 | Duncker et al. |
| 2014/0341921 A1* | 11/2014 | Honda et al. |
| 2015/0246090 A1 | 9/2015 | Knippels et al. |

FOREIGN PATENT DOCUMENTS

| | | |
|---|---|---|
| EP | 1714660 A1 | 10/2006 |
| RU | 002137837 C1 * | 9/1999 |

OTHER PUBLICATIONS

Stefka et al., "Commensal bacteria protect against food allergen sensitization", Proceedings of the National Academy of Sciences, vol. 111, No. 36, Aug. 25, 2014, pp. 13145-13150.
Cao et al., "The role of commensal bacteria in the regulation of sensitization to food allergens", FEBS Letters, vol. 588, No. 22, May 1, 2014, pp. 4258-4266.
Veereman-Wauters et al., "Physiological and Bifidogenic Effects of Prebiotic Supplements in Infant Formulae", Archives of Disease in Childhood, vol. 91, No. 6, Jun. 1, 2011, pp. 763-771.
Moro et al., "A mixture of prebiotic oligosaccharides reduces the incidence of atopic dermatitis during the first six months of age", Archines of Disease in Childhood, vol. 91, No. 10, Oct. 1, 2006, pp. 814-819.
International Search Report issued in PCT/EP2017/064233, dated Sep. 14, 2017.
Written Opinion of the International Searching Authority issued in PCT/EP2017/064233, dated Sep. 14, 2017.

* cited by examiner

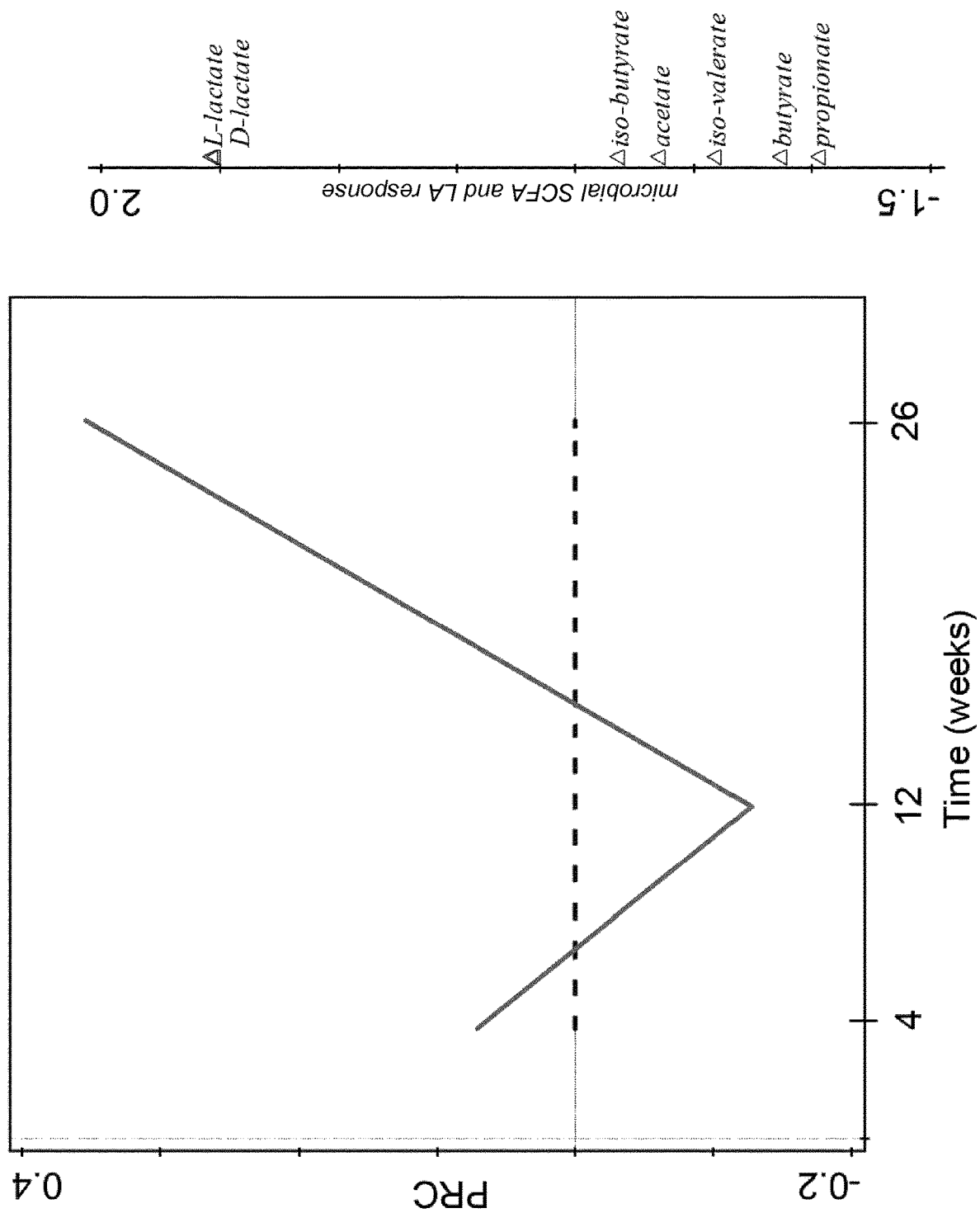

RISK OF ALLERGY AND NUTRITION TO REDUCE THAT RISK

CROSS-REFERENCE TO RELATED APPLICATIONS

This application is the National Phase of International Patent Application No. PCT/EP2017/064233, filed Jun. 12, 2017, published on Dec. 14, 2017 as WO 2017/212064 A1, which claims priority to European Application No. 16174039.4, filed Jun. 10, 2016. The contents of these applications are herein incorporated by reference in their entirety.

FIELD OF THE INVENTION

The present invention is in the field of allergy, in particular eczema, and concerns a method to assess early in life the risk of developing allergy. Also the invention concerns nutritional remedies to reduce the risk of allergy.

BACKGROUND OF THE INVENTION

Early gut microbial development is a dynamic process that may influence human health throughout life. Aberrations in this process have been associated with the development of allergic diseases, but exact microbial patterns remain unclear. The gradual diversification towards a relatively stable adult-like composition is a dynamic process influenced by environmental factors such as birth mode, gestational age at birth and early life nutrition. The importance of pioneering microbes is particularly clear as alterations in the colonization process have been associated with the rise of allergic disorders in affluent societies. Studies so far point into the direction that the gut microbiota of allergic infants exhibit an accelerated ecological succession to a community structure more typical of adults. Allergic diseases in their different manifestations comprise the most common chronic disease in childhood in developed countries. Atopic dermatitis is typically the first allergic manifestation with a sequential onset to other allergic manifestations, a process known as the allergic march, also called the atopic march.

First facultative anaerobic bacteria that grow fast on simple sugars, such as Enterobacteriaceae, are gradually replaced by anaerobic bacteria, such as the genera *Bifidobacterium* and *Bacteroides*. The microbiota further diversifies with the introduction of solid foods to the infant diet at 4-6 months of age, which establishes more strict anaerobes, such as the adult-type Clostridium clusters IV and XIVa. The succession of species and establishment of a stable adult-type community in early life is guided by human milk and may be critically important, both from microbial composition and activity point of view, as in view of the concurrent maturation of the immune system. This early colonization and succession is thought to form a crucial process laying the foundation for optimal health later in life.

Breastfeeding is thought to protect against the development of allergy, as numerous allergens and immune mediators present in human milk are absent from artificial milks, as well as the high abundance of human milk oligosaccharides. Several studies have been performed with different types of infant formulas (IF) supplemented with non-digestible oligosaccharides, known as prebiotics. Prebiotics are typically non-digestible fibres that reach the colon intact and are known to selectively stimulate the growth and activity of specific beneficial members of the microbiota. Significant reductions in eczema risk were observed in intervention trials with IF supplemented with specific prebiotic oligosaccharides (Arslanoglu et al., 2012, J Biol Regulation & Homeostatic Agents 26:49-59; Grüber et al., 2010, J Allergy and Clinical Immunology 126:791-797; Moro et al., 2006, Archives of Disease in Childhood 91:814-819.

WO 2009/102199 discloses compositions comprising bifidobacteria and galacto-oligosaccharides and fructo-oligosaccharides that support the introduction of solid weaning foods in the diet of infants that receive infant milk formula or breast milk. US 2015/0352162 discloses compositions, particularly baby food compositions, comprising live lactate utilizing propionic acid producing bacteria, as well as viable lactic acid producing bacteria, its manufacture and use in the treatment of digestive diseases. US 2014/0341921 discloses species of human-derived bacteria belonging to the Clostridia class that induce accumulation of regulatory T cells (Treg cells) in the colon and suppress immune functions, and pharmaceutical compositions containing these bacteria for use in preventing and treating immune-mediated diseases such as autoimmune diseases.

SUMMARY OF THE INVENTION

In a clinical trial with infants at risk for atopic disease the development of faecal microbiota composition and its metabolites was analyzed in the first 6 months of life. In infants that had or had not developed eczema when 18 months of age, the differences in intestinal microbiota compositions and development thereof earlier in life was investigated. Infants that had an incidence of eczema by the age of 18 months showed a decreased acquisition of lactate-utilizing bacteria, in particular of *Eubacterium* and *Anaerostipes* at 26 weeks of age. Furthermore in these infants the amount of faecal lactic acid was low at 4 and 12 weeks of age, but increased at 26 weeks of age, when the infants started receiving complementary feeding (introduction to solid food). In infants that did not develop eczema this pattern was reversed, in that the amount of lactic acid was decreased at week 26 compared to the earlier time points.

This study indicates for the first time a link between the functionality of the microbiota and the expression of allergic phenotypes in infants, in particular eczema. These observations indicate that the type of microbial succession of species and metabolite cross-feeding at specific developmental stages in early life, in particular during weaning when the infant is introduced to solid food and a more adult type diet, have long term health effects on the immune system. The accumulation of lactic acid and/or a relative low number of lactate utilizing bacteria at 26 weeks of age, can therefore be a predictor for the risk of developing eczema later in life. Furthermore, these observations aid the development of optimal nutritional strategies to support gut colonization of lactic acid utilizing bacteria when the infant has an age of about 6 months or above. Subsequently, of a large range of fibres tested in in vitro fermentation experiments, only a few fibres, namely inulin, polydextrose and partially hydrolysed guar gum were able to stimulate the growth of the lactate utilizing bacteria *Anaerostipes* spp. Therefore nutritional supplements or follow on formula or young children formula comprising these fibres together with lactate utilizing bacteria can help to redirect the microbiota and its metabolism to one more similar to healthy infants not developing eczema later in life.

DETAILED DESCRIPTION

Thus in one aspect, the invention concerns a nutritional composition comprising lactate utilizing bacteria and at least one fibre selected from the group consisting of polyfructose with an average DP of 10 or higher, polydextrose with an average DP of 10 or higher and partially hydrolysed guar gum with an average DP of 10 or higher. Preferably the nutritional composition is for administration to an infant or young child.

The invention also concerns a method for preventing allergy or reducing the risk of allergy by administering a nutritional composition comprising lactate utilizing bacteria and at least one fibre selected from the group consisting of polyfructose with an average DP of 10 or higher, polydextrose with an average DP of 10 or higher and partially hydrolysed guar gum with an average DP of 10 or higher, to an infant or young child. For certain jurisdictions, this can also be worded as the use of bacteria and fibre in the preparation of a nutritional composition for administration to an infant or young child for preventing allergy or reducing the risk of allergy, wherein the bacteria are lactate utilizing bacteria and the fibre is at least one fibre selected from the group consisting of polyfructose with an average DP of 10 or higher, polydextrose with an average DP of 10 or higher and partially hydrolysed guar gum with an average DP of 10 or higher. The invention can also be worded as a nutritional composition, which is preferably for administration to an infant or young child, comprising lactate utilizing bacteria and at least one fibre selected from the group consisting of polyfructose with an average DP of 10 or higher, polydextrose with an average DP of 10 or higher and partially hydrolysed guar gum with an average DP of 10 or higher for use in preventing allergy or reducing the risk of allergy. Thus in other words, the invention concerns a nutritional composition comprising lactate utilizing bacteria and at least one fibre selected from the group consisting of polyfructose with an average DP of 10 or higher, polydextrose with an average DP of 10 or higher and partially hydrolysed guar gum with an average DP of 10 or higher for use in preventing allergy or reducing the risk of allergy by administering the nutritional composition to an infant or young child.

In a preferred embodiment the nutritional composition according to the invention, or in the method or use according to the invention, the lactate utilizing bacteria are selected from the group consisting of *Anaerostipes* and *Eubacterium*.

The invention also concerns a method for preventing allergy or reducing the risk of allergy by administering a nutritional composition comprising at least one fibre selected from the group consisting of polyfructose with an average DP of 10 or higher, polydextrose with an average DP of 10 or higher and partially hydrolysed guar gum with an average DP of 10 or higher to an infant or young child. For certain jurisdictions, this can also be worded as the use of fibre in the preparation of a nutritional composition for administration to an infant or young child for preventing allergy or reducing the risk of allergy, wherein the fibre is at least one selected from the group consisting of polyfructose with an average DP of 10 or higher, polydextrose with an average DP of 10 or higher and partially hydrolysed guar gum with an average DP of 10 or higher. The invention can also be worded as a nutritional composition, which is preferably for administration to an infant or young child, comprising at least one fibre selected from the group consisting of polyfructose with an average DP of 10 or higher, polydextrose with an average DP of 10 or higher for use preventing allergy or reducing the risk of allergy. In this embodiment, the nutritional composition preferably further comprises lactate utilizing bacteria. Preferably the lactate utilizing bacteria are selected from the group consisting of *Anaerostipes* and *Eubacterium*.

In a preferred embodiment of the present invention, the nutritional composition is for administering to or for use in an infant or young child that is at enhanced risk of developing allergy.

In a preferred embodiment the infant or young child that is at enhanced risk of developing allergy is identified by determining the concentration and/or percentage of lactic acid based on total organic acids in faecal material obtained from the infant or young child
  a. at a first time point when the infant or young child is about 3 to 17 weeks old, and
  b. at a second time point when the infant or young child is about 20 to 35 weeks old, and
  c. subsequently determining whether the concentration and/or percentage of lactic acid based on total organic acid in the faecal material has increased or decreased from the first to the second time point,
wherein an increase in lactic acid indicates an enhanced risk for developing allergy in the infant or young child, and/or by determining the amount or relative amount of lactate utilizing bacteria in faecal material obtained from the infant or young child
  a. at a first time point when the infant or young child is about 3 to 17 weeks old, and
  b. at a second time point when the infant or young child is about 20 to 35 weeks old, and
  c. subsequently determining whether the amount or relative amount of lactate utilizing bacteria has increased or decreased from the first to the second time point,
wherein a minimal increase or a decrease in the amount or in the relative amount of lactate utilizing bacteria indicates an enhanced risk for developing allergy in the infant or young child.

In one aspect the invention also concerns a method for assessing whether an infant is at enhanced risk for developing allergy, comprising determining the concentration and/or percentage of lactic acid based on total organic acids in faecal material obtained from the infant
  a. at a first time point when the infant is about 3 to 17 weeks old, and
  b. at a second time point when the infant is about 20 to 35 weeks old, and
  c. subsequently determining whether the concentration and/or percentage of lactic acid based on total organic acid in the faecal material has increased or decreased from the first to the second time point,
wherein an increase in lactic acid indicates an enhanced risk for developing allergy in the infant.

Likewise, the invention also concerns a method for assessing whether an infant is at enhanced risk for developing allergy, comprising determining the amount or relative amount of lactate utilizing bacteria in faecal material obtained from the infant or young child
  a. at a first time point when the infant is about 3 to 17 weeks old, and
  b. at a second time point when the infant is about 20 to 35 weeks old, and
  c. subsequently determining whether the amount or relative amount of lactate utilizing bacteria has increased or decreased from the first to the second time point,
wherein a minimal increase or a decrease in the amount or in the relative amount of lactate utilizing bacteria indicates an enhanced risk for developing allergy in the infant.

In all aspects and embodiments of the present invention, the allergy preferably is eczema.

Microbiota and its Metabolites

It was found that the amount, or relative amount, of lactate utilizing bacteria was decreased in the microbiota of infants at the age of 26 weeks, of infants that developed allergy, in particular eczema, when compared to infants that did not develop allergy. In particular the amount and the relative amount of *Anaerostipes* and *Eubacterium* was decreased. *Anaerostipes* is a genus belonging to the family of Lachnospiraeceae, is strictly anaerobic and is a member of the human intestinal microbiota. It can use lactic acid as a carbon and energy source and produces mainly butyric acid. Known species of *Anaerostipes* are *A. caccae, A butyraticus A. hadrus* and *A. rhamnosivorans. Eubacterium* is a genus belonging to the family of Eubacteriaceaea, is strictly anaerobic and some of the species are member of the human intestinal microbiota. In particular *Eubacterium limosum* and *Eubacterium hallii* are known to utilize lactate usually producing butyrate. In the present method for assessing whether an infant is at enhanced risk for developing allergy, preferably the amount or relative amount of lactate utilizing bacteria is the amount or relative amount of lactate utilizing butyrate producing bacteria. In the present method for assessing whether an infant is at enhanced risk for developing allergy, preferably the amount of lactate utilizing bacteria is the total of the amount of *Anaerostipes* spp and *Eubacterium* spp. Preferably it is the total of the amount of *Anaerostipes caccae, Anaerostipes butyraticus, Anaerostipes hadrus, Anaerostipes rhamnosivorans, Eubacterium limosum* and *Eubacterium hallii*. In one embodiment in the present method for assessing whether an infant is at enhanced risk for developing allergy, preferably the amount of lactate utilizing bacteria is the total of the amount of *Anaerostipes* spp, preferably the total of the amount of *Anaerostipes caccae, Anaerostipes butyraticus, Anaerostipes hadrus* and *Anaerostipes rhamnosivorans*. In one embodiment in the present method for assessing whether an infant is at enhanced risk for developing allergy, preferably the amount of lactate utilizing bacteria is the total of the amount of *Eubacterium* spp, preferably the total of the amount of *Eubacterium limosum* and *Eubacterium hallii*. In the context of the present invention a minimal increase in the amount of lactate utilizing bacteria means an increase of less than 0.1% based on total bacteria. A minimal increase in the relative amount of lactate utilizing bacteria means an increase of less than 0.1%. Other lactate utilizing bacteria are *Coprococcus catus* and *Veillonella* sp. These bacteria mainly produce propionate from lactate.

It was found that the amount and relative amount, or concentration and percentage, of D- and L-lactic acid was increased in the faecal material of microbiota of infants of the age of 26 weeks that developed allergy, in particular eczema, when compared to infants that did not develop allergy. At earlier age this was reversed and the amount of lactic acid was lower at the age of 4 and 12 weeks or younger in infants that developed allergy. The increased levels of acetate and lactate, early in life, at 4 and 12 weeks in infants that did not develop allergy, may be crucial for the establishment of the lactate utilizing bacteria around 6 months of age. This is indicative that microbial succession of species and metabolite cross-feeding at specific developmental stages in early life are essential in establishing a gut community and environment that supports the immune system. Aberrant temporal dynamics up to 26 weeks of age in infants developing allergy in the first 18 months of life regarding microbiota (lactate utilizing bacteria) and its metabolites (levels of lactic acid) was observed. Therefore, remedies to improve these dynamics towards the dynamics as found in infants not developing allergy, in particular eczema, can be designed. Hence in one embodiment the invention relates to nutritional compositions comprising lactate utilizing bacteria, preferably lactate utilizing butyrate producing bacteria, preferably *Anaerostipes* spp and *Eubacterium* spp, more preferably at least one selected from *Anaerostipes caccae, Anaerostipes butyraticus, Anaerostipes hadrus, Anaerostipes rhamnosivorans, E hallii* and *E. limosum*. In one embodiment, preferably the *Anaerostipes* is *Anaerostipes caccae*. These species can be isolated from human faeces as known in the art, or can be ordered from culture collections. The lactic acid utilizing bacteria can be cultured and dried as known in the art. Preferably a nutritional composition comprising lactic acid utilizing bacteria comprises $10^2$ to $10^9$ cfu lactate utilizing bacteria per g dry weight, more preferably $10^3$ to $10^6$ cfu.

Fibres that Stimulate Growth of Lactic Acid Utilizing Bacteria

In one embodiment the invention relates to a method to increase the amount or relative amount of lactate utilizing bacteria, preferably lactate utilizing butyrate producing bacteria, preferably *Anaerostipes* and/or *Eubacterium*, in the intestinal microbiota of an infant or young child, said method comprising the administration of at least one fibre selected from the group consisting of polyfructose with an average DP of 10 or higher, polydextrose with an average DP of 10 or higher and partially hydrolysed guar gum with an average DP of 10 or higher to said infant or young child.

The term 'degree of polymerisation' (DP) as used herein means number of monomer units joined together in the poly- or oligomer. The term "soluble" as used herein, when having reference to a polysaccharide, fibre or oligosaccharide, means that the substance is at least 50% soluble according to the method described by Prosky et al., J Assoc Off Anal Chem, 1988, 71:1017-1023. An average degree of polymerization refers to the average degree of polymerization based on weight.

Preferably fibre selected from the group consisting of polyfructose with an average DP of 10 or higher, polydextrose with an average DP of 10 or higher and partially hydrolysed guar gum with an average DP of 10 or higher is present in a nutritional composition in an amount of 0.2 to 8 g based on 100 g dry weight, more preferably 0.5 to 5 gram based on 100 g dry weight of the nutritional composition.

According to a particularly preferred embodiment, partially hydrolysed guar gum (PHGG) is used as a fibre to stimulate lactic acid utilizing bacteria or to prevent allergy. Guar gum is a polysaccharide obtainable from the endosperm of *Cyamopsis tetragonolobus* and contains mainly high molecular weight hydrocolloidal polysaccharide, composed of galactose and mannose units combined through glycosidic linkages. Specifically, the guar gum preferably consists of linear chains of (1→4) beta-D-mannopyranosyl units with alpha-D-galactopyranosyl units attached by (1→6) linkages. PHGG is commercially available under the tradename Benefiber® from Novartis Nutrition Corporation or under the tradename "Sunfiber® AG" from Taiyo Kagaku. Preferably, the hydrolysed gum is in an agglomerated form, which has better solubility. The DP is typically between 10 and 300. Preferably the DP is between 20 and 150, even more preferably between 25 and 100.

The fibre selected from polyfructose, polydextrose and partially hydrolysed guar gum in the present nutritional composition preferably comprises 0.2 to 8 grams, even more preferably 0.5 to 5 grams partially hydrolysed guar gum, based on 100 g dry weight of the nutritional composition.

According to a particularly preferred embodiment, polyfructose is used as a fibre to stimulate lactic acid utilizing bacteria or to prevent allergy. The term polyfructose, or fructopolysaccharide, refers to a polysaccharide carbohydrate comprising a chain of at least 10 β-linked fructose units with a DP between 10 and 300, preferably between 20 and 300. Preferably inulin is used. Inulin is e.g. available under the tradename "Raftilin HP®", (Orafti). The term "inulin" is used herein to refer to glucose-terminated fructose chains with at least 90% fructose units having a DP between 10 and 300. Inulin can be described as $GF_n$, wherein G represents a glucosyl unit, F represents a fructosyl unit and n is the number of fructosyl units linked to each other, n being 9 or more. A small part of the inulin molecules, however, may have no terminal glucose unit, due to hydrolysis during processing. The average DP of the fructopolysaccharide is preferably at least 10, more preferably at least 15, more preferably at least 20 or more, up to 300. In inulin the fructose units are linked with a $\beta(2\rightarrow1)$ linkage. The fibre selected from polyfructose, polydextrose and partially hydrolysed guar gum in the present nutritional composition preferably comprises 0.2 to 8 grams, even more preferably 0.5 to 5 grams fructopolysaccharides, based on 100 g dry weight of the nutritional composition.

According to a particularly preferred embodiment, polydextrose is used as a fibre to stimulate lactic acid utilizing bacteria or to prevent allergy. Polydextrose, or indigestible polydextrin, refer to digestion-resistant (malto)dextrins or digestion-resistant polydextrose, or indigestible starch which have a DP of 10 to 50, preferably between 10 and 20. Polydextrose is at least 75% indigestible, preferably at least 90% indigestible. These polydextrose are preferably produced by a combination of hydrolysis and transglucosidation reactions. In a preferred embodiment, the polydextroses comprise all $\alpha(1\rightarrow4)$, $\alpha(1\rightarrow6)$ glucosidic bonds and $1\rightarrow2$ and $1\rightarrow3$ linkages. Polydextroses are for example available under the tradename "Fibersol 2®" from Matsutami Inductries, "Sta-Lite®" Polydextrose from Tate and Lyle, Novelose 330®" from Ingredion, or Litesse® from Danisco. The fibre selected from polyfructose, polydextrose and partially hydrolysed guar gum in the present nutritional composition preferably comprises 0.5 to 8 grams, even more preferably 1 to 5 gram digestion resistant polydextrose, based on 100 g dry weight of the nutritional composition.

Macronutrients

The present composition preferably contains 5 to 16 en % protein; 35 to 60 en % fat; and 25 to 75 en % carbohydrates, preferably 5 to 12.0 en % protein; 39 to 50 en % fat; and 40 to 55 en % digestible carbohydrates. The term "en %" is short for energy percentage and represents the relative amount each constituent contributes to the total caloric value of the preparation. For example 40 en % digestible carbohydrates equals 10 g of carbohydrates per 100 kcal, as 1 g of carbohydrates has 4 kcal.

The composition preferably contains 1.4 to 6 g of a protein source per 100 ml. The composition comparably contains 8.5 to 19 g per 100 g dry weight. The protein source may comprise intact protein, hydrolysed proteins, peptides or free amino acids or mixtures thereof. Suitable protein sources are cow's milk protein, casein, whey and soy protein. The protein content is based on the Kjeldahl percentage, N*6.38.

The composition preferably further contains 2.1 to 6.5 g fat per 100 ml, containing 0.3 to 1.5 g linoleic acid (LA) per 100 ml, at least 50 mg α-linolenic acid (ALA) per 100 ml, in which the ratio of LA/ALA ranges from of 5 to 15. Based on dry weight the composition preferably contains 12.5 to 30 g fat, 1.8 to 12.0 g LA, and at least 0.30 g ALA per 100 g, in which the ratio of LA/ALA ranges from 5 to 15. The amount of saturated fatty acids is preferably between 10 and 58 wt. % of total fatty acids, the concentration of monounsaturated fatty acids ranges from 17 to 60% based on weight of total fatty acids and the concentration of polyunsaturated fatty acids ranges from 11 to 36% based on weight of total fatty acids. These amounts and ratios of ALA and LA have the advantage that a balanced biosynthesis of n-3 and n-6 polyunsaturated fatty acids is achieved. Preferably the present composition contains long chain polyunsaturated fatty acids (LC PUFA), such as eicosapentaenoic acid (EPA), docosahexaenoic acid (DHA) and arachidonic acid (AA). Suitable lipid sources are milk fats, canola oil, safflower oil, sunflower oil, olive oil, coconut oil, marine oils, etc. or fractions or mixtures thereof comprising suitable fatty acids.

The present composition preferably contains 6 to 19 g digestible carbohydrates per 100 ml, more preferably 6-19 gram lactose.

Nutritional Composition

The present composition is preferably administered in liquid form. In order to meet the caloric requirements, the composition preferably contains 50 to 200 kcal/100 ml, more preferably 60 to 90 kcal/100 ml. Preferably the composition is in a liquid form, with a viscosity below 35 cps. When suitable, the composition is in a powdered form, which can be reconstituted with water to from a liquid. Preferably the nutritional composition according to the present invention or in the method or use according to the present invention is a follow on formula or a young child formula.

Application

An aberrant temporal dynamics up to 26 weeks of age in infants developing allergy, in particular eczema, in the first 18 months of life regarding microbiota, preferably lactate utilizing bacteria, and its metabolites, preferably lactic acid, was observed. Therefore, these dynamics can be used to assess the risk of the infant to improve these dynamics towards the dynamics as found in infants not developing allergy, in particular eczema, can be designed.

Hence in one embodiment the invention relates to a method of assessing whether an infant is at enhanced risk for developing allergy, the method comprising determining the concentration and/or percentage of lactic acid based on total organic acids in faecal material obtained from said infant at about 20 to 35 weeks of age, preferably about 26 weeks of age, and at an earlier time point, when the infant is about 3 to 17 weeks of age, preferably about 4 to 12 weeks of age, preferably at 4 and/or 12 weeks of age. The infant has an increased risk for allergy when the amount, e.g. concentration, and/or percentage of D-lactic acid, L-lactic acid, or the sum of D- and L-lactic acid, is higher at the time point of 20 to 35 weeks, preferably about 26 weeks of age, when compared to earlier time points, most preferably at 4 and/or 12 weeks of age. The infant has an increased risk for allergy when the amount of L-lactic acid, is above 10 mmol/kg faeces at the time point of 20 to 35 weeks, preferably about 26 weeks of age. The infant has an increased risk for allergy when the relative amount of D-lactic acid, L-lactic acid, or the sum of D- and L-lactic acid is higher at the time point of 20 to 35 weeks, preferably about 26 weeks of age, when compared to earlier time points, when the infant is about 3 to 17 weeks of age, preferably about 4 to 12 weeks of age most preferably at 4 and/or 12 weeks of age. The amount of lactic acid in the faeces or colon refers to the concentration of lactic acid in the faeces or colon, e.g. mol/kg or mol/l. The relative amount of lactic acid relates to the percentage of moles of lactic acid based on total organic acids, being the sum of D- and L-lactic acid, acetic acid, propionic acid, butyric acid, valeric acid, isobutyric acid and isovaleric acid. The infant has an increased risk for allergy when the relative amount of L-lactic acid, is above 10% at the time point of 20 to 35 weeks, preferably about 26 weeks of age.

Hence in one embodiment the invention relates to a method of assessing whether an infant is at enhanced risk for developing allergy, the method comprising determining the amount or relative amount of lactate utilizing bacteria, preferably lactate utilizing butyrate producing bacteria, preferably *Anaerostipes* and/or *Eubacterium* in faecal material obtained from said infant at about 20 to 35 weeks of age, preferably about 26 weeks of age, and at an earlier time point, when the infant is about 3 to 17 weeks old, preferably about 4 to 12 weeks of age, preferably at 4 weeks of age. Preferably the total amount of *Anaerostipes caccae, Anaerostipes butyraticus, Anaerostipes hadrus, Anaerostipes rhamnosivorans, E hallii* and *E. limosum* is determined. The infant has an increased risk for allergy when the amount of lactate utilizing bacteria is lower, or has minimally increased, at the time point of 20 to 35 weeks, preferably about 26 weeks of age, when compared to earlier time points, when the infant is about 3 to 17 weeks of age, preferably about 4 to 12 weeks of age most preferably at 4 weeks of age. The amount of bacteria relates to the amount of bacteria per ml faeces. Amount of bacteria can also be concentration, or abundance. Relative amount and relative abundance relates to the percentage of a specific group of bacteria based on total bacteria.

In one embodiment the invention relates to a method for preventing allergy or decreasing the risk of allergy by administering lactate utilizing bacteria or fibres that stimulate lactate utilizing bacteria or both. These fibres and bacteria have been described above in more detail. Alternatively the invention relates to the administration of one or more fibres selected from the group consisting of polyfructose with an average DP of 10 or higher, polydextrose with an average DP of 10 or higher and partially hydrolysed guar gum with an average DP of 10 or higher to simulate the amount of lactate utilizing bacteria.

Allergy relates to allergic disease, and is a condition caused by hypersensitivity of the immune system to something in the environment that usually causes little problem in most people. Allergic diseases include hay fever, food allergies, atopic dermatitis, rhinitis and allergic asthma. In particular allergy was determined based on its skin symptoms. In a preferred embodiment allergy is eczema. In yet a further preferred embodiment, eczema includes one or more of allergic eczema, allergic dermatitis and allergic eczema dermatitis syndrome (AEDS). Eczema can be diagnosed based on 2 out of 3 positive scores according to the modified Hanifin and Rajka criteria (Kunz et al., 1997, Dermatology 195(1):10-19).

As the timing of lactate accumulation and lactate utilizing bacteria depletion is very relevant, the methods or nutritional compositions of the present invention are preferably administered to infants that are starting to being introduced to complementary feeding or solid food. The diversification of the infant diet around the time of weaning not only marks the gradual diversification towards an adult gut microbiota, but also exposes the infant to an increasing level of antigens from the diet, which requires the immune system to adequately respond to these harmless substances while safeguarding defense against potential pathogens. The establishment of lactate utilizing bacteria around 6 months of age, e.g. at about 26 weeks, may prove important for establishing and maintaining homeostasis with our immune system during this critical stage of development. Hence, in one embodiment of the method or use according to the invention, the nutritional composition is administered to or for administration to an infant and wherein the infant is being introduced to complementary feeding or solid food.

As the timing of lactate accumulation and lactate utilizing bacteria depletion is very relevant, the methods or nutritional compositions of the present invention are preferably administered to infants that are about 5 to 18 months of age, more preferably 6 to 12 months of age. This corresponds to the age of weaning.

DESCRIPTION OF THE FIGURE

The FIGURE shows Principal Response Curves representing the changes in bacterial metabolites, i.c. levels of short chain fatty acids (SCFA) and lactic acids, across time and its interaction with developing eczema.

EXAMPLES

Example 1: Aberrant Temporal Dynamics in Infants Developing Eczema in the First 18 Months of Life; Decreased Microbial Conversion of Lactic Acid in Infants Developing Eczema Faecal samples were taken when infants were 4, 12 and 26 of age. Faecal samples were collected by the parents into 10 ml stool containers (Greiner Bio-One, Kremsmünster, Austria), immediately frozen ($-12°$ C. to $-20°$ C.) and transported within three months in a cold storage bag with ice-packs to the hospital. Upon arrival at the hospital and prior to evaluation at the laboratory, samples were kept and transported at ultra-low temperatures ($-75°$ C. to $-85°$ C.).

Frozen stool samples were defrosted on ice and were ten times diluted in PBS buffer (150 mM NaCl, 10 mM $Na_2HPO_4$, 20 mM $NaH_2PO_4$, pH 7.4) and homogenized by the addition of 5 to 10 glass beads (3 mm in diameter) and vortexing for 3 min. Glass beads and larger particles were removed by centrifugation at 300×g for 1 min. Several 1 ml portions of the homogenized suspension were stored at ultra-low temperatures until further processing and analysis.

Faecal suspensions were thawed on ice and centrifuged for 10 minutes at 14.000×g. Next, 350 µl supernatant was heated for 10 minutes at 100° C. to inactivate all enzymes and centrifuged again. A portion of the supernatant was used to quantitatively determine the SCFA acetic, propionic, n-butyric, isobutyric, isovaleric and n-valeric acids by gas chromatography. Another portion of the supernatant was used to enzymatically analyze the levels of lactate using a D-/L-lactic acid assay kit (Megazyme, Wicklow, Ireland).

16S rRNA-gene sequencing was used to characterize the microbiota composition of faeces collected at 4 and 26 weeks of age in a set of vaginally born infants, including breastfed infants (BF, n=30) and infants receiving the experimental formula (n=51) or control formula (n=57). Diagnosis of eczema at the age of 18 months was based on 2 out of 3 positive scores according the modified Hanifin and Rajka criteria (Kunz et al., 1997, Dermatology 195(1):10-19). Of these 138 infants 52 infants had developed eczema when 18 month of age. Faecal samples for microbial analysis were selected with the following criteria: (I) infants were selected from the breastfed reference group and from the key group of interest (KGI), which consisted of those infants that started formula before 4 weeks of age, (II) when born vaginally and (III) if stool specimens were available at 4, 12 and 26 weeks of age.

Faecal suspensions were thawed on ice and 200 µl of each suspension was mixed with 450 µl of extraction buffer (100 mM Tris-HCl, 40 mM EDTA, pH 9.0) and 50 µl of 10% sodium dodecyl sulfate. Phenol-chloroform extractions combined with bead-beating were subsequently performed as described by Matsuki, et al., 2004, Appl Environ Microbiol 70:167-173 except that DNA was re-suspended in 0.1 ml of TE (10 mM Tris-HCl, 1 mM EDTA, pH 8.0). The V3-V5 regions of the 16S rRNA gene were amplified using the forward primer 357F, and a 'bifidobacteria-optimised' reverse primer 926Rb. The reverse primers included a 12 base-pair error-correcting Golay barcode. PCR was carried out in quadruplicate as previously described in Sim et al., 2012, PLoS One 7: e32543). Replicate amplicons were pooled and purified and three 454 Life Sciences GS FLX (Roche, Branford, Conn., USA) pyrosequencing runs were carried out following the Roche Amplicon Lib-L protocol.

The 'Quantitative Insights Into Microbial Ecology' (QIIME) v1.5.0 package was used to analyse shotgun processed data (Caporaso et al, 2010, Nat Methods 7: 335-336). Sequencing data was first denoised using AmpliconNoise followed by chimera-removal with Perseus (Quince et al, 2011, BMC Bioinformatics 12: 38). Alignment was carried out using the SILVA rRNA database (SSU_REF108) (Pruesse et al, 2007 Nucleic Acids Res 35: 7188-7196) for reference and clustered at 97% sequence identity into operational taxonomic units (OTUs) using the UCLUST algorithm (Edgar, 2010 Bioinformatics 26: 2460-2461). Rarefaction was performed and sequences present only once in the dataset (singletons) were removed.

The statistical analyses of the 16S rRNA-gene markers (frequencies of OTUs) and bacterial metabolite data (levels of SCFAs and lactate) were performed using Canoco 5 software (Šmilauer and Lepš., 2014, Multivariate Analysis of Ecological Data using CANOCO 5, 2nd ed. edn. Cambridge University Press: Cambridge Books Online) and differential abundance testing using the R-package MetagenomeSeq (Paulson et al., 2013, Nat Meth 10:1200-1202). The OTU count data were first aggregated at the genus level, resulting in a total of 142 genera, normalized by total sum scaling and log-transformed. Genera that were present in less than 10 samples were discarded to account for the sparsity of the data. This resulted in 58 taxonomic features that were used as input for the statistical analyses performed. Canoco 5 was used to model the taxonomic data using constrained ordination methods and Monte Carlo permutation tests (MCPT) to evaluate the explanatory power of sample covariates (Ter Braak, 1986, Ecology 67: 1167-1179; Van den Brink and Ter Braak, 1999, Environmental Toxicology and Chemistry 18: 138-148) with significance at 0.05. The sample covariates identified were subsequently used in all models and comparisons. Benjamini-Hochberg false-discovery rate (FDR) was used to account for multiple comparisons (Benjamini and Hochberg, 1995 Journal of the Royal Statistical Society Series B (Methodological) 57: 289-300) with significance for adjusted P-values (P-adj) at 0.05.

Constrained ordination methods combined with forward selection of variables in Canoco 5 was used to identify the sample covariates that explained most of the variation in microbial taxonomic composition (Legendre and Legendre, 2012 Numerical ecology, vol. 24. Elsevier: Amsterdam; Ter Braak, 1986). The approach of forward selection identified age (in weeks), feeding group (formula 1, 2 or breastfed reference group), ethnicity (Asian, caucasian or other) and having siblings (yes or no) as significantly influencing the bacterial taxonomic composition of the fecal samples (with Benjamini-Hochberg method to control for false-discovery rate with significance at 0.05). The sample covariates identified were subsequently used in all models and comparisons, either as explanatory variables or as covariates with significance for adjusted P-values (P-adj) at 0.05.

Principal Response Curves (PRC) and the Monte Carlo Permutation test (MCPT with 499 permutaions and significance at 0.05) were used to assess the effects of developing eczema on the bacterial metabolites (SCFA and lactic acids) over time (Van den Brink and Ter Braak, 1999). Differential abundant bacterial genera were evaluated using MetagenomeSeq with Benjamini Hochberg false discovery rates with significance at 0.05.

Univariate data analysis were performed using GraphPad Prism version 6.02 for Windows (GraphPad Software, La Jolla, California, USA) applying Mann-Whitney test for two-group comparisons and Kruskall-Wallis with Dunn's multiple comparisons test for three or more groups with significance at 0.05.

Results

The amount of faecal lactate in time is shown in table 1. At 4 and 12 weeks the amount of lactic acid tended to be lower in the infants that developed eczema, but the difference was not statistically different. At 26 weeks however, the amount of D and L-lactic acid was significantly higher in infants that developed eczema. A similar result was observed when the lacic acid was expressed as % of the total organic acids (the sum of D-lactic acid, L-lactid acid, acetic acid butyric acid, propionic acid, valeric acid, isobutyric acid and isovaleric acid), see table 2.

The effect of developing eczema on the fecal bacterial metabolite composition over time was investigated using Principal Response Curves (PRC, Van den Brink and Ter Beek, 1999), while correcting for all significant covariates identified. Significant temporal differences on the first constrained axis produced were observed for the interaction. The differential dynamics were most pronounced from 12 to 26 weeks of age. Infants developing eczema were characterized by decreased levels of both isomers of lactate at 12 weeks, a pattern which was subsequently reversed at 26 weeks of age. In the FIGURE the horizontal axis represents time and the vertical axis the PRC score values. Infants not developing eczema (NO ECZEMA; dashed line - - - - - - ) were used as reference level and has zero PRC values and so its curve lays over the horizontal axis. The change for infants developing eczema in the first 18 months of life (ECZEMA; solid line —) is shown as a response curve relative to this reference. The microbial response scores are shown on the separate vertical (one-dimensional) plot. The multiple of the PRC score with the response score provides a quantitative interpretation as well as the direction of the microbial change at the respective time points (4, 12 and 26 weeks) in infants developing eczema as compared to those that did not. Result of the PRC analysis for faecal SCFA and LA are shown for the first PRC set, which was significant for the interaction (MCPT: P=0.034, explained variation 84.4%, 499 permutations).

TABLE 1

D-lactic acid and L-lactic acid in mmol per kg of wet weight faeces

| Age | Lactic acid | Statistics | NO ECZEMA | ECZEMA | Summary |
|---|---|---|---|---|---|
| 4 weeks | D-lactic acid | n | 83 | 48 | ns |
| | | Mean | 2.36 | 2.78 | |
| | | Median (Q1-Q3) | 0.020 (0.020-2.92) | 0.020 (0.020-4.34) | |
| | L-lactic acid | n | 83 | 48 | ns |
| | | Mean | 11.1 | 7.30 | |
| | | Median (Q1-Q3) | 0.020 (0.020-9.88) | 2.30 (0.020-9.62) | |
| 12 weeks | D-lactic acid | n | 81 | 49 | ns |
| | | Mean | 3.83 | 3.35 | |
| | | Median (Q1-Q3) | 0.020 (0.020-4.17) | 0.020 (0.020-4.27) | |
| | L-lactic acid | n | 81 | 49 | ns |
| | | Mean | 10.2 | 6.75 | |
| | | Median (Q1-Q3) | 0.020 (0.020-14.4) | 0.020 (0.020-9.64) | |
| 26 weeks | D-lactic acid | n | 86 | 52 | ** |
| | | Mean | 2.33 | 5.39 | |
| | | Median (Q1-Q3) | 0.020 (0.020-2.11) | 0.020 (0.020-9.28) | |
| | L-lactic acid | n | 86 | 52 | * |
| | | Mean | 7.74 | 14.3 | |
| | | Median (Q1-Q3) | 0.020 (0.020-7.88) | 4.37 (0.020-24.2) | | n = number of non-missing subjects, Q1 = 25% quartile and Q3 = 75% quartile. Statistical summary is based on Kruskall-Wallis with Dunn's multiple comparisons test comparing infants with eczema versus infants without at the same age (ns = $P > 0.05$, * = $P \leq 0.05$, ** = $P \leq 0.01$)

The effect of developing eczema on the fecal bacterial metabolite composition over time was investigated using Principal Response Curves (PRC, Van den Brink and Ter Beek, 1999), while correcting for all significant covariates identified. Significant temporal differences on the first constrained axis produced were observed for the interaction. The differential dynamics were most pronounced from 12 to 26 weeks of age. Infants developing eczema were characterized by decreased levels of both isomers of lactate at 12 weeks, a pattern which was subsequently reversed at 26 weeks of age. In the FIGURE the horizontal axis represents time and the vertical axis the PRC score values. Infants not developing eczema (NO ECZEMA; dashed line - - - - - -) were used as reference level and has zero PRC values and so its curve lays over the horizontal axis. The change for infants developing eczema in the first 18 months of life (ECZEMA; solid line —) is shown as a response curve relative to this reference. The microbial response scores are shown on the separate vertical (one-dimensional) plot. The multiple of the PRC score with the response score provides a quantitative interpretation as well as the direction of the microbial change at the respective time points (4, 12 and 26 weeks) in infants developing eczema as compared to those that did not. Result of the PRC analysis for faecal SCFA and LA are shown for the first PRC set, which was significant for the interaction (MCPT: P=0.034, explained variation 84.4%, 499 permutations).

TABLE 2

Relative abundance of D-lactic acid and L-lactic acid as mol % of total organic acids measured

| Age | Lactic acid | Statistics | NO ECZEMA | ECZEMA | Summary |
|---|---|---|---|---|---|
| 4 weeks | D-lactic acid | n | 83 | 48 | ns |
| | | Mean | 2.88 | 4.19 | |
| | | Median (Q1-Q3) | 0.080 (0.030-0.58) | 0.145 (0.040-8.24) | |
| | L-lactic acid | n | 83 | 48 | ns |
| | | Mean | 9.93 | 9.35 | |
| | | Median (Q1-Q3) | 0.100 (0.030-14.7) | 4.63 (0.0525-12.9) | |
| 12 weeks | D-lactic acid | n | 81 | 49 | ns |
| | | Mean | 4.26 | 3.39 | |
| | | Median (Q1-Q3) | 0.060 (0.030-5.89) | 0.060 (0.030-6.51) | |
| | L-lactic acid | n | 81 | 49 | ns |
| | | Mean | 10.7 | 7.41 | |
| | | Median (Q1-Q3) | 0.200 (0.030-15.7) | 0.120 (0.030-12.2) | |
| 26 weeks | D-lactic acid | n | 86 | 52 | *** |
| | | Mean | 1.96 | 4.61 | |
| | | Median (Q1-Q3) | 0.025 (0.020-2.52) | 1.90 (0.030-8.58) | |
| | L-lactic acid | n | 86 | 52 | ** |
| | | Mean | 7.97 | 11.8 | |
| | | Median (Q1-Q3) | 0.030 (0.020-8.03) | 5.51 (0.030-18.6) | | n = number of non-missing subjects, Q1 = first quartile and Q3 = third quartile. Statistical summary is based on Kruskall-Wallis with Dunn's multiple comparisons test comparing infants with eczema versus infants without eczema at the same age (ns = $P > 0.05$, * = $P \leq 0.05$,  = $P \leq 0.01$, * = $P \leq 0.001$)

So, at 26 weeks of age the level and percentage of lactic acid was higher in the faeces of infants that had developed eczema at 18 months compared to infants that had not developed eczema at 18 months, and also the level and percentage of faecal lactic acid was increased when compared to the earlier time points of 4 and 12 weeks. In infants that did not develop eczema on the other hand the faecal lactate levels were lower at 26 weeks when compared with the earlier time points.

TABLE 3

Relative abundance (%) of *Eubacterium* spp

| Age | Statistics | NO ECZEMA | ECZEMA | Summary |
|---|---|---|---|---|
| 4 weeks | n | 82 | 48 | ns |
| | Mean | 0.00780 | 0.599 | |
| 26 weeks | n | 86 | 52 | ns |
| | Mean | 0.275 (1.15) | 0.0996 | |
| Difference | n (sample pairs) | 82 | 48 | * |
| 26 weeks – 4 weeks | Mean | 0.280* (1.17) | −0.507 | | n = number of non-missing subjects; Statistical summary is based on Kruskall-Wallis with Dunn's multiple comparisons test comparing infants with eczema versus infants without eczema at the same age (ns = $P > 0.05$, * = $P \leq 0.05$,  = $P \leq 0.01$, * = $P \leq 0.001$)

TABLE 4

Relative abundance (%) of *Anaerostipes* spp

| Age | Statistics | NO ECZEMA | ECZEMA | Summary |
|---|---|---|---|---|
| 4 weeks | n | 82 | 48 | ** |
| | Mean | 0.00171 | 0.245 | |
| 26 weeks | n | 86 | 52 | ns |
| | Mean | 0.434 | 0.314 | |
| 26 weeks – 4 weeks | n (sample pairs) | 82 | 48 | # |
| | Mean | 0.350 | 0.0942 | | n = number of non-missing subjects; Statistical summary is based on Kruskall-Wallis with Dunn's multiple comparisons test comparing infants with eczema versus infants without eczema at the same age (ns = $P > 0.05$, # = $P \leq 0.1$, ** = $P \leq 0.01$)

MetagenomeSeq was used to assess differential abundances of bacterial taxa over time in infants developing and not developing eczema, as well as the taxa being differential over time comparing the two groups, while correcting for the covariates identified. The increases over time observed for *Eubacterium* and *Anaerostipes* spp. were more pronounced for infants not developing eczema as compared to infants developing eczema, see tables 3 and 4. Both genera are associated with a specialist group of microbes known to convert lactate together with acetate into mainly butyrate, hence referred to as lactate-utilizing bacteria (LUB). The levels of lactic acid and presence lactic acid utilizing bacteria were indeed inversely correlated.

The increased levels of acetate and lactate, and decreased amounts of propionate and butyrate, early in life, at 4 and 12 weeks, before starting weaning, may be crucial for the establishment of LUB like *Eubacterium* and *Anaerostipes* spp. around 6 months of age, as observed in this study for subsequent infants not developing eczema in contrast to infants developing eczema.

In conclusion, this study indicates for the first time a link between the functionality of the microbiota and the expression of allergic phenotypes in early life. It emphasizes the importance of the early life microbial succession of species and metabolite cross-feeding to develop a gut physiology that supports gut development, but also the development of normal immune responses towards environmental triggers. These observations could aid the development of optimal nutritional strategies to support timely gut colonization of keystone species in the gradually diversifying infant gut.

Example 2: L-lactate Accumulation in Faeces of Infants that Develop Allergy

To gain insights into the development of gut microbiota in initially healthy infants who develop allergy in early life and identify plausible microbiota biomarkers of allergic disease, a nested case-control study of Chinese infants from a large Singaporean birth cohort was performed. The maturation of intestinal microbiota and its metabolism was measured in 20 pair-matched allergic cases and non-allergic controls during the first 6 months of life using 16S rRNA sequencing. The allergic infants were assessed by means of cumulative incidence of clinical allergy symptoms (eczema episode/ allergic rhinitis/food allergy) and SCORAD values; according to the study eczema workflow up to 12 months of age. At age of 6 months higher levels of faecal L-lactate (12.25 mmol/kg wet weight faeces) were detected in infants that were allergic at 12 months of age, compared to the L-lactic acid level in infants that did not develop allergy (3.95 mmol/kg wet weight faeces), $P<0.05$. L-Lactic acid levels in the group of allergic infants were higher at 6 months when compared to week 3 and month 3, which is indicative for lactate accumulation in this group. For non allergic infants it was the other way around and the amount of faecal L-lactic acid was higher at week 3 and month 3.

TABLE 5

L-lactic acid in mmol per kg of wet weight faeces

| Faecal L-lactic acid | NO ECZEMA | | ECZEMA | |
|---|---|---|---|---|
| (mmol/kg ww faeces) | Month 3 | Month 6 | Month 3 | Month 6 |
| L-lactic acid | 9.50 | 3.95 | 6.55 | 12.25 |

Example 3: Selection of Fibres that Stimulate Lactate Utilizing Bacteria

Fresh faecal samples were collected from four healthy adults, pooled, and divided in smaller portions mixed with glycerol (10%) in an anaerobic cabinet and stored at −80° C. Before the experiment the faecal samples were defrosted and mixed with the fermentation medium in 1:5 in a falcon tube and a t=0 sample was taken, 6 ml of this suspension was added to falcon tube with the substrate of interest and mixed. This mixed suspension was put in a dialysis tube and the dialysis tube was added in a 100 ml bottle filled with 100 ml dialysis medium. Bottles were closed and incubated at 37° C. A fermentation with no added carbohydrates acted as a negative control (blanc), whereas fermentation with glucose served as a positive control. Fibres and glucose were added at concentrations of 200 mg per 6 ml of faeces suspension.

19 single fibres and 3 fibre mixtures were tested. Fermentation was at 37° C. at 48 h under anaerobic conditions. Starting pH of the buffer was 6.3.

Preservative medium: buffered peptone 20.0 g/l, L-cysteine-HCl 0.5 g/l, sodium thioglycollate 0.5 g/l, resazurine tablet 1 per litre, adjusted to pH 6.7±0.1 with 1 M NaOH or HCl. Boiled in microwave. Filled into 30 ml serum bottles with 25 ml medium. Sterilised 15 minutes at 121° C.

McBain & MacFarlane medium: buffered peptone water 3.0 g/l, yeast extract 2.5 g/l. mucin (brush borders) 0.8 g/l, tryptone 3.0 g/l, L-cysteine-HCl 0.4 g/l, bile salts 0.05 g/l, $K_2HPO_4 \cdot 3H_2O$ 2.6 g/l, $NaHCO_3$ 0.2 g/l, NaCl 4.5 g/l, $MgSO_4 \cdot 7H_2O$ 0.5 g/l, $CaCl_2$ 0.228 g/l, $FeSO_4 \cdot 7H_2O$ 0.005 g/l. Filled into 500 ml Scott bottles with the medium and sterilised 15 minutes at 121° C.

Buffered medium: $K_2HPO_4 \cdot 3H_2O$ 2.6 g/l, $NaHCO_3$ 0.2 g/l, NaCl 4.5 g/l, $MgSO_4 \cdot 7H_2O$, 0.5 g/l, $CaCl_2$ 0.228 g/l, $FeSO_4 \cdot 7H_2O$ 0.005 g/l. Adjusted to pH 6.3±0.1 with $K_2HPO_4$ or $NaHCO_3$. Filled into 500 ml Scott bottles with the medium and sterilised 15 minutes at 121° C. Faecal suspension: the preserved solution of faeces was centrifuged at 13,000 rpm for 15 minutes. The supernatant was removed and the faeces was mixed with the McBain & Mac Farlane medium in a weight ratio of 1:5.

Faecal sample was stored in an RNAlater solution (Ambion, Courtaboef, France) for subsequent bacteria DNA or RNA isolation. The faecal sample was homogenized and the volume of RNAlater was adjusted to achieve a final faecal solution of 1:10. 200 µl of this 10-fold dilution was added to 1 ml of PBS buffer and centrifuged for 5 min at 5000 g. The supernatant was discarded and the pellet stored at −80° C. Faecal DNA and RNA was extracted. Determination of bacteria abundance was determined based on the quantification of RNA molecules using primers targeting mainly 16S rRNA sequences. In order to have a common scale of comparison with other bacterial quantification methods, the number of detected molecules (RNA or DNA) was given as cell equivalents (CE), for which a bacteria culture of a reference strain was used as a standard curve.

For determination of the target bacteria present in the faecal samples, three serial 10-fold dilutions of the extracted RNA or DNA sample were applied to qPCR or RT-qPCR, and CT values in linear range of the assay were applied to the standard curve generated in the same experiment to obtain the corresponding bacterial count in each nucleic acid sample, and then converted to the count per sample. Different species of bacteria were analysed amongst which there was one lactate utilizing bacteria, *Anaerostipes caccae*. Statistical analysis was performed using the Mann Whitney method.

Results

At t=0 the amount of *Anaerostipes caccae* was equivalent to $2*10^8$ cfu/ml. Upon 48 h of fermentation with glucose the amount had doubled to $4*10^8$ cfu/ml.

Of the 19 different fibres and 3 fibre mixes tested, a substantial increase in *Anaerostipes caccae* compared with the controls T=48 h (glucose) was observed with the following fibres: Orafti® GR (Beneo), an inulin with a DP>10 (5-fold), Orafti® HP (Beneo), a long chain inulin with an average DP of >23 (5 fold), Benefiber® (Novartis) a partially hydrolysed guar gum (PHGG) (4 fold), Sta-Lite® (Tate and Lyle) a polydextrose with DP>10 (5 fold) and Novelose® 330 (national starch) a resistant starch (3 fold). One fibre mixture, rich in inulin, also stimulated the growth of *A. caccae*.

No increase or even a decrease compared to the glucose control was observed with the other fibres tested, e.g the short chain FOS Actilight® (Meiji) and Frutalose® (Orafti both having an average DP<5. Table 6 shows the positive results for polyfructose with an average DP of 10 or higher, polydextrose with an average DP of 10 or higher and partially hydrolysed guar gum with an average DP of 10 or higher. For comparison the result of non-positive short chain fructooligosdacchrides in included.

TABLE 6

Increase of *A. caccae* upon faecal fermentation of several fibres.

| t | Fibre | Log | Log increase relative to t = 48 glucose |
|---|---|---|---|
| T = 0 | blanc | 8.3 | — |
| T = 48 | glucose | 8.6 | 0 |

TABLE 6-continued

Increase of *A. caccae* upon faecal fermentation of several fibres.

| t | Fibre | Log | Log increase relative to t = 48 glucose |
|---|---|---|---|
| T = 48 | Orafti ® HP | 9.3 | 0.7 |
| T = 48 | Orafti ® GR | 9.3 | 0.7 |
| T = 48 | Actilight ® | 8.7 | 0.1 |
| T = 48 | Novelose ® 330 | 9.1 | 0.5 |
| T = 48 | Sta-Lite ® | 9.3 | 0.7 |
| T = 48 | Benefiber ® | 9.2 | 0.6 |

The invention claimed is:

1. A method of preventing allergy or reducing the risk of allergy in an infant or young child, wherein the infant or young child is at enhanced risk of developing allergy, comprising administering to the infant or young child a nutritional composition, comprising lactate utilizing bacteria and at least one fibre selected from the group consisting of polyfructose with an average DP of 10 or higher, poly dextrose with an average DP of 10 or higher and partially hydrolysed guar gum with an average DP of 10 or higher, wherein the infant or young child that is at enhanced risk of developing allergy is identified by determining the concentration and/or percentage of lactic acid based on total organic acids in faecal material obtained from the infant or young child
   a. at a first time point when the infant or young child is about 3 to 17 weeks old, and
   b. at a second time point when the infant or young child is about 20 to 35 weeks old, and
   c. subsequently determining whether the concentration and/or percentage of lactic acid based on total organic acid in the faecal material has increased or decreased from the first to the second time point,
wherein an increase in lactic acid indicates an enhanced risk for developing allergy in the infant or young child and wherein the allergy is eczema.

2. A method of preventing allergy or reducing the risk of allergy in an infant or young child, wherein the infant or young child is at enhanced risk of developing allergy, comprising administering to the infant or young child a nutritional composition, comprising lactate utilizing bacteria and at least one fibre selected from the group consisting of polyfructose with an average DP of 10 or higher, poly dextrose with an average DP of 10 or higher and partially hydrolysed guar gum with an average DP of 10 or higher, wherein the infant or young child that is at enhanced risk of developing allergy is identified by determining the amount or relative amount of lactate utilizing bacteria in faecal material obtained from the infant or young child
   a. at a first time point when the infant or young child is about 3 to 17 weeks old, and
   b. at a second time point when the infant or young child is about 20 to 35 weeks old, and
   c. subsequently determining whether the amount or relative amount of lactate utilizing bacteria has increased or decreased from the first to the second time point,
wherein a decrease in the amount or relative amount of lactate utilizing bacteria indicates an enhanced risk for developing allergy in the infant or young child and wherein the allergy is eczema.

3. The method according to claim 2, wherein the amount of lactate utilizing bacteria is the total of the amount of *Anaerostipes* and *Eubacterium*.

4. A method for assessing whether an infant is at enhanced risk for developing eczema, comprising determining the concentration and/or percentage of lactic acid based on total organic acids in faecal material obtained from the infant
   a. at a first time point when the infant or young child is about 3 to 17 weeks old, and
   b. at a second time point when the infant or young child is about 20 to 35 weeks old, and
   c. subsequently determining whether the concentration and/or percentage of lactic acid based on total organic acid in the faecal material has increased or decreased from the first to the second time point, wherein an increase in lactic acid indicates an enhanced risk for developing eczema in the infant.

5. A method for assessing whether an infant is at enhanced risk for developing eczema, comprising determining the amount or relative amount of lactate utilizing bacteria in faecal material obtained from the infant or young child
   a. at a first time point when the infant or young child is about 3 to 17 weeks old, and
   b. at a second time point when the infant or young child is about 20 to 35 weeks old, and
   c. subsequently determining whether the amount or relative amount of lactate utilizing bacteria has increased or decreased from the first to the second time point, wherein a decrease in the amount or relative amount of lactate utilizing bacteria indicates an enhanced risk for developing eczema in the infant.

6. The method according to claim 5, wherein the amount of lactate utilizing bacteria is the total of the amount of *Anaerostipes* and *Eubacterium*.

* * * * *